United States Patent [19]
Polovnikov et al.

[11] 4,213,346
[45] Jul. 22, 1980

[54] METHOD AND APPARATUS FOR TESTING CYCLICALLY OPERATED MECHANICAL MEMBERS FOR DEFECTS

[76] Inventors: Sergei V. Polovnikov, dom 3, kv. 207; Anatoly M. Zaznobin, dom 22, kv. 9, both of Krasnoobsk Novosibirskoi oblasti; Gennady F. Masalov, 1 Televizionny pereulok, 7, Novosibirsk; Alexandr A. Mischenkov, dom 3, kv. 24, Krasnoobsk Novosibirskoi oblasti, all of U.S.S.R.

[21] Appl. No.: 949,376

[22] Filed: Oct. 6, 1978

[30] Foreign Application Priority Data

Dec. 5, 1977 [SU] U.S.S.R. .............................. 2551865

[51] Int. Cl.$^2$ ............................................. G01N 29/04
[52] U.S. Cl. .................................................... 73/660
[58] Field of Search ................................. 73/660, 593

[56] References Cited

U.S. PATENT DOCUMENTS

| | | | |
|---|---|---|---|
| 3,012,434 | 12/1961 | Wehof | 73/660 |
| 3,699,806 | 10/1972 | Weichbrodt | 73/593 |
| 3,731,526 | 5/1973 | Games | 73/660 |
| 3,783,680 | 1/1974 | Mason | 73/660 |

*Primary Examiner*—Anthony V. Ciarlante

*Attorney, Agent, or Firm*—Steinberg and Blake

[57] ABSTRACT

A method for testing cyclically operated mechanical members for defects comprises the steps as follows: a frequency range of at least two wideband electrical signals corresponding to the defects of the test member is selected; the modulus and phase of the resultant electrical signals is determined and the magnitude is accumulated using the value of the phase of that signal within a given number of rotational cycles of the test member; defect locations are determined using the maximal accumulated magnitudes of the resultant electrical signal and their corresponding phases. An apparatus to realize the disclosed method comprises at least two vibration pickups adapted to sense the vibration of the test member and coupled to the inputs of adjustable pass band filters which are operated to select a frequency range corresponding to the defects of the test member. The outputs of the filters are coupled to the inputs of a resultant electrical signal magnitude computing unit which is coupled to the input of a summing analyzer. The latter has another input coupled to a resultant electrical signal phase detector. There are also two position pickups adapted to determined the position of the test member and coupled to the resultant electrical signal phase detector.

3 Claims, 1 Drawing Figure

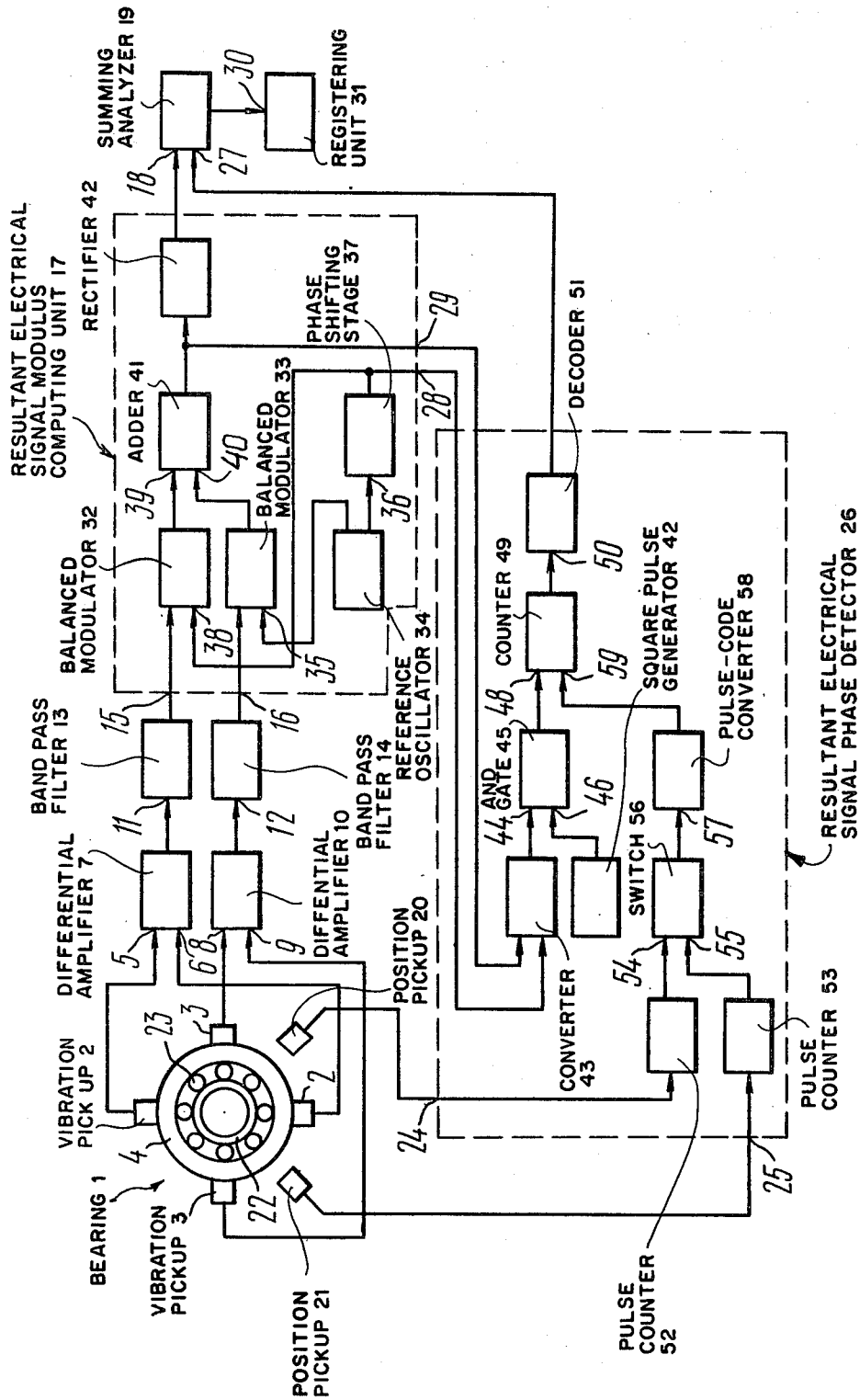

METHOD AND APPARATUS FOR TESTING CYCLICALLY OPERATED MECHANICAL MEMBERS FOR DEFECTS

The invention relates to a field concerned with testing and diagnosis of cyclically operated mechanical members, and more particularly to a method and apparatus for testing such members for defects.

The disclosed method and apparatus are generally suitable for detecting defects encountered in ball bearings and gear wheels, for determining beats of shafts, and for balancing rotors and rotatable parts.

The prior art methods for testing cyclically operated mechanical members, based on the analysis of acoustic vibrations of test objects, provide a low validity with which the location of defects is determined in members being rotated asynchronously with respect to the rotation of the driving shaft; this also relates to cases where a test member moves along a complex path. To provide for a greater validity with which the defects can be located, it is necessary to build apparatus capable of handling acoustic vibrations in such a manner that both their intensity and vectorial direction are taken into account.

Known in the art is a method for testing cyclically operated mechanical members for defects comprising the steps as follows: a vibration signal from the test member is converted to a wideband electrical signal from which an electrical signal is extracted which has a frequency range corresponding to the defects of the test member, the selected electrical signal being accumulated, the values characteristic of the angular positions of the test member being converted to another electrical signal, and the last two signals being used to determine location of the defects of the test member.

In the described method, the electrical signal selected from the wideband signal and having a frequency range characteristic of the defects of the test member is then rectified and the rectified signal is accumulated.

The known method possesses a low validity of determining defect locations since the magnitude of the resultant vibration signal is not determined in this case and the summing analyzer accumulates the signal without taking into account the phase of the magnitude. It is therefore impossible to detect defects in parts which perform asynchronous movement as related to the rotation of the driving shaft. For example, when rolling bodies pass a defect on either the outer or inner race of a ball bearing several times, then the number of peaks in the signal accumulated by the summing analyzer does not correspond to the number of defects available.

Known in the art is a device for testing cyclically operated mechanical members for defects (cf. British Pat. No. 1,367,773, cl. G01M 13/00 G01H 1/00, datec Oct. 6, 1971) comprising a vibration pickup adapted to sense the vibration of the test member and electrically coupled to the input of an adjustable band pass filter which extracts a frequency range corresponding to the defects of the test member and has its output coupled to an input of a summing analyzer having another input coupled to a position pickup adapted to determine the position of the test member.

The known device utilizes a single vibration pickup adapted to convert a vibration signal to an electrical signal, while a synchronous operation of the summing analyzer is attained using the data on the angular position of the driving shaft only. The device offers a low validity of determining defect locations since the operating axis of the vibration pickup is held at a certain angle. If vibration propagates in a direction which does not coincide with the operating axis of the vibration pickup, then information loss takes place due to a decreased level of the signal at the pickup output. The peak level of the signals accumulated by the summing analyzer, which are characteristic of the member defects, is therefore decreased too.

Synchronization of the summing analyzer according to the angular position of the driving shaft generally results in a condition in which the number of defects differs from that of peaks in the signal accumulated by the summing analyzer, thereby giving a low validity of determining defect locations.

An object of the invention is to provide a method and apparatus for testing cyclically operated mechanical members for defects, ensuring a higher validity with which defect locations are detected.

Another object of the invention is to provide for testing cyclically operated mechanical members for defects obeying a certain distribution in the test member.

There is disclosed a method for testing cyclically operated mechanical members comprising converting a vibration signal produced by a cyclically operated mechanical member under test to a wideband electrical signal, extracting an electrical signal with a frequency range corresponding to the defects of the test member from the wideband electrical signal, accumulating the selected electrical signals, converting data on the angular position of the test member to another electrical signal, and determining the location of the defects of the test member using these electrical signals, which method comprises, according to the invention, converting a vibration signal from the test member to at least another wideband electrical signal, extracting an electrical signal with a frequency range corresponding to the defects of the test member from said latter wideband electrical signal, and determining the magnitude and the phase of the resultant electrical signal using the two selected electrical signals, the magnitude of the resultant electrical signal being accumulated using the values of the phase of that signal within a given number of rotational cycles of the test member, and the location of the defects being detected using the maximal accumulated magnitudes of the resultant electrical signal and their corresponding phases.

Advantageously, the method should comprise subtracting, performed after the determination of the magnitude and the phase of the resultant electrical signal, the value of the electrical signal characteristic of the angular position of the test member from the value of the electrical signal characteristic of the phase of the resultant electrical signal, the magnitude of the resultant electrical signal being accumulated using the values of the difference of the electrical signals characteristic of the phase of the resultant electrical signal and the angular position of the test member.

There is disclosed an apparatus for testing cyclically operated mechanical members for defects to realize the proposed method, comprising a vibration pickup adapted to sense the vibration of the test member and electrically coupled to the input of an adjustable band pass filter operated to select a frequency range corresponding to the defects of the test member and having its output electrically coupled to an input of a summing analyzer which has a second input coupled to a position pickup adapted to determine the position of the test member, and has its output coupled to a registering unit, which apparatus comprises, according to the invention, at least one additional vibration pickup adapted to sense the vibration of the test member and having its operating axis disposed at 90° to the operating axis of the first vibration pickup, adjustable band pass filters each having its input coupled to a respective vibration pickup, a resulting electrical signal magnitude computing unit having its inputs coupled to the outputs of the adjustable band pass filters and having its output coupled to the input of the summing analyzer, at least one additional position pickup adapted to determine the position of the test member, and a resultant electrical signal phase detector having its inputs coupled to the outputs of the position pickups and to second and third outputs of the resultant electrical signal computing unit, and having its output coupled to the second input of the summing analyzer.

Since the disclosed method incorporates a step for determining the magnitude of the resultant electrical signal loss of information is avoided in cases where the direction of the vibration signal vector does not coincide with the operating axis of the vibration pickups. Another step deals with the accumulation of the modulus of the resultant electrical signal using the values of the phase of that signal within a given number of rotational cycles of the test member. This makes it possible to reveal periodical variations of the magnitude of the resultant electrical signal, related to a distribution of defects in the test member and observed against a background depicting random signal variations not related to the defects. As a result, the validity of determining defect locations is increased.

The apparatus to realize the disclosed method includes subassemblies in which the steps of the method are performed. It comprises several measurement channels with which no loss of information takes place in cases where the vector of the vibration signal does not coincide with the operating axis of the vibration pickup. Using several position pickups makes it possible to determine the vibration vector in a coordinate system for movable members. The resultant electrical signal magnitude computing unit allows for combining data from several measurement channels and for greater validity of determinating defect locations.

The invention will now be described, by way of example, with reference to an accompanying drawing, which shows a block diagram of an apparatus for testing cyclically operated mechanical members for defects, according to the invention.

The apparatus of the invention comprises four vibration pickups 2, 3 mounted on a bearing 1 and adapted to sense the vibration of a cyclically operted mechanical member under test. The vibration pickups 2, 3 are installed on an outer race 4 of the bearing 1 and have their operating axes arranged at right angles to each other. Two vibration pickups 2, in diametrically spaced relationship, are coupled to inputs 5, 6 of a differential amplifier 7, while two vibration pickups 3, in diametrically spaced relationship too, are coupled to inputs 8,9 of a differential amplifier 10.

The outputs of the differential amplifiers 7,10 are coupled to inputs 11,12 of adjustable band pass filters 13, 14 which operates to select a frequency range corresponding to the defects of the test member. The outputs of the filters 13,14 are coupled to respective inputs 15,16 of a resultant electrical signal magnitude computing unit 17 which has its output coupled to an input 18 of a summing analyzer 19.

In the described embodiment, the apparatus of the invention comprises two position pickups 20,21 adapted to sense the position of the test member. The pickup 20 is adapted to check the position of an inner race 22 of the bearing 1, whereas the pickup 21 is used to check the position of the rolling bodies which are balls 23 of the bearing 1. The outputs of the position pickups 20,21 are coupled to respective inputs 24,25 of a resultant electrical signal phase detector 26 which has its output coupled to an input 27 of the summing analyzer 19.

Second and third outputs 28,29 of the computing unit 17 are coupled to the inputs of the unit 26. The output of the summing analyzer 19 is coupled to an input 30 of a registering unit 31 which is a recorder in the described embodiment. An oscilloscope, a computer or a digital printer may be used as the registering unit 31.

The computing unit 17 comprises, in the described embodiment, balanced modulators 32,33 having their first inputs used as the inputs 15,16 of the unit 17. The latter also includes a reference oscillator 34 which has an output coupled to a second input 35 of the balanced modulator 33, and has another output coupled to an input 36 of a phase-shifting stage 37. The output of the phase-shifting stage 37 is coupled to a second input 38 of the balanced modulator 32 and is used as the output 28 of the computing unit 17. The outputs of the balanced modulators 32,33 are coupled to inputs 39,40 of an adder 41 whose output is coupled to the input of a rectifier 42 and is used as the output 29 of the computing unit 17. The output of the rectifier 42 serves as the output of the computing unit 17 coupled to the input 18 of the summing analyzer 19.

In the described embodiment, the unit 26 comprises a converter 43 adapted to convert electrical signal phase shifts to time intervals and having its first input used as an input of the unit 26 coupled to the output 28 of the computing unit 17, and having its second input used as an input of the unit 26 coupled to the output 29 of the computing unit 17. The output of the converter 43 is coupled to a first input 44 of an AND gate 45 which has its second input 46 coupled to the output of a square pulse generator 47. The output of the AND gate 45 is coupled to a first input 48 of a counter 49 whose output is coupled to an input 50 of a decoder 51. The output of the decoder 51 is used as the output of the unit 26 coupled to the input 27 of the summing analyzer 19.

The unit 26 comprises a pulse counter 52 whose input is used as the input 24 of the unit 26 and also comprises a pulse counter 53 whose input is used as the input 25 of the unit 26. The outputs of the pulse counters 52,53 are coupled to inputs 54,55 of a switch 56 controlled by the human operator. The output of the switch 56 is coupled to an input 57 of a pulse-code converter 58 which has its output coupled to a second input 59 of the counter 49.

The apparatus of the invention operates in the following manner. The rotation of the inner race 22 of the bearing 1 causes the immovable outer race 4 to produce oscillations characterized by a vector whose magnitude and direction are dependent upon the presence, location and value of defects in the bearing 1. The coordinate systems related to the inner race 4, the outer race 22 and the bearing cage provide a means for measuring the magnitude and phase of the resultant electrical signal; therefore, those angular positions of the vibration signal vector are determined in one of the coordinate systems with which the vector assumes peak magnitudes and the most frequently encountered angular positions of the vector are also determined with the result that defect locations are detected.

The vibration pickups 3 respond to the vibration component read along the abscissa and respective signals are delivered to the inputs 8,9 of the differential amplifier 10, while the signals from the vibration pickups 2 responding to the vibration component read along the ordinate are delivered to the inputs 5,6 of the differential amplifier 7.

The outputs of the differential amplifiers 7,10 produce signals passed to the inputs 11,12 of the adjustable band pass filters 13,14 which operate to select a frequency range corresponding to the defects of the test member.

The signals from the outputs of the filters 13,14 are applied to the inputs 15,16 of the computing unit 17, which serve as the first control inputs of the balanced modulators 32,33. The second input 35 of the balanced modulator 33 accepts a reference sine voltage from the reference oscillator 34. The second input 38 of the balanced modulator 32 accepts a reference voltage from the phase-shifting stage 37 which is shifted by 90°.

The modulated signals from the outputs of the balanced modulators 32,33 are applied respectively to the inputs 39,40 of the adder 41 in which the signals are subject to quadrature summation.

The output of the adder 41 produces an r.f. signal whose amplitude is proportional to the modulus of the resultant electrical signal and whose phase provides information about the angular position of the resultant electrical signal.

The r.f. signal comes to the input of the rectifier 42 and is then transferred to the input 18 of the summing analyzer 19 for further accumulation.

The first input of the converter 43 accepts a signal from the output of the phase-shifting stage 37, whereas the second input of the converter 43 receives a signal from the adder 41. The converter 43 produces a signal delivered to the first input 44 of the AND gate 45 whose second input 46 receives signals from the square pulse generator 47. The AND gate 45 is used to switch over the signals from the output of the square pulse generator 47 to the first input 48 of the counter 49.

When the defects are detected using a movable coordinate system, a case where the pickups 2,3 are mounted on the outer race 4 of the bearing 1 to detect the defects belonging to the inner race 22 or balls 23, a difference between the electrical signals characteristic of the phase of the resultant electrical signal and of the angular position of the test member is determined.

The counter 49 operates as follows, After a counting cycle is terminated, the counter 49 is reset to zero and receives immediately a preset codeword from the pulse-code converter 58. When the human operator operates the switch 56 to connect its input 54 to the output of the counter 52, the counter 49 receives a codeword describing the angular position of the inner race 22. With the input 55 of the switch 56 connected to the counter 53, a codeword providing information about the angular position of the balls 23 is stored in the counter 49.

After the counter 49 is given a preset codeword, it receives pulses from the square pulse generator 47, passed through the AND gate 45. When the coordinate system of the immovable outer race 4 is used, no preset codeword is introduced in the counter 49.

The output of the counter 49 produces a codeword corresponding to the angular position of the resultant electrical signal, related to either the movable or the immovable coordinate system depending upon the operator's discretion.

The counter 52 receives pulses characteristic of the angular position of the test member and available from the position pickup 20 within a single revolution of the inner race 22. When a counting cycle is terminated, the counter 52 is reset to zero. The counter 53 receives pulses characteristic of the angular position of the test member and available from the position pickup 21 within a single revolution of the bearing cage. When a counting cycle is terminated, the counter 53 is reset to zero.

The codeword produced by the counter 49 and corresponding to the angular position of the resultant electrical signal determined in either the immovable or the movable coordinate system is applied to the input 50 of the decoder 51 which produces control signals delivered to the second input 27 of the summing analyzer 19 and used to switch over the storage locations of the latter.

In the "output" operating mode, the output of the summing analyzer 19 provides the magnitude of the resultant electrical signal accumulated using the phase of the latter and delivered to the input 30 of the registering unit 31 (a recorder).

What is claimed is:
1. A method for testing cyclically operated mechanical members for defects, comprising the steps of
   converting vibration signals produced by a cyclically operated mechanical member under test to at least two wideband electrical signals;
   extracting from the wideband electrical signals electrical signals having a frequency range corresponding to defects of the test member;
   converting the angular position of the test member to a position electrical signal;
   determining the magnitude and phase of a resultant electrical signal using two selected wideband electrical signals;
   accumulating the magnitude of the resultant electrical signal using the values of the phase of that signal within a given number of rotational cycles of the test member; and
   determining the location of the defects of the test member using the maximal accumulated magnitudes of the resultant electrical signal and their corresponding phases.

2. A method as claimed in claim 1, further comprising the steps of
   subtracting, after the determination of the magnitude and the phase of the resultant electrical signal, the value of the electrical signal characteristic of the angular position of the test member from the value of the electrical signal characteristic of the phase of the resultant electrical signal; and
   accumulating the magnitudes of the resultant electrical signal using the values of the difference of the electrical signals characteristic of the phase of the resultant electrical signal and the angular position of the test member.

3. A device for testing cyclically operated mechanical members for defects, said device comprising
   at least two vibration pickups adapted to sense the vibration of a cyclically operated mechanical member under test, said vibration pickups having operating axes arranged at right angle to each other, mounted on said test member, and each having an output;

a plurality of adjustable band pass filters adapted to select a frequency range corresponding to the defects of the test member, each having inputs coupled to said outputs of said vibration pickups and each having an output;

a resultant electrical signal modulus computing unit having a plurality of inputs equal in number to said adjustable band pass filters and coupled to said outputs of said adjustable band pass filters, said computing unit having three outputs;

a summing analyzer having two inputs and an output, the first input of said summing analyzer being coupled to a first output of said three outputs of said resultant electrical signal modulus computing unit;

a registering unit having an input coupled to said output of said summing analyzer;

at least two position pickups adapted to determine the position of the test member, said position pickups being mounted on the test member and each having an output; and a resultant electrical signal phase detector having a plurality of inputs, two of said inputs of said signal phase detector being coupled to two outputs of said resultant electrical signal modulus computing unit, said signal phase detector having an output coupled to said second input of said summing analyzer, respective inputs of said resultant electrical signal phase detector being coupled to said outputs of said position pickups.

* * * * *